(12) United States Patent
Sawada

(10) Patent No.: US 6,255,555 B1
(45) Date of Patent: *Jul. 3, 2001

(54) TRANSGENIC MOUSE EXPRESSING HUMAN FUSIN AND HUMAN CD4

(75) Inventor: Shinichiro Sawada, Ibaraki (JP)

(73) Assignee: Japan Science and Technology Corporation (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/061,048

(22) Filed: Apr. 16, 1998

(30) Foreign Application Priority Data

Apr. 17, 1997 (JP) .................................................... 9-100615

(51) Int. Cl.$^7$ .......................... C12N 15/00; C12N 15/11; C12N 15/63

(52) U.S. Cl. ............................. 800/18; 800/13; 800/21; 800/25; 435/320.1; 536/23.1

(58) Field of Search ................................. 800/2, 3, 11, 24, 800/13, 18, 21; 536/23.1; 435/320.1

(56) References Cited

FOREIGN PATENT DOCUMENTS

| 2 692 435 | 12/1993 | (FR) . |
|---|---|---|
| WO 94 06908 | 3/1994 | (WO) . |
| WO 94 28915 | 12/1994 | (WO) . |
| WO 97 08303 | 3/1997 | (WO) . |
| WO 97 28258 | 8/1997 | (WO) . |

OTHER PUBLICATIONS

Berson et al., "A Seven–Transmembrane Domain Receptor Involved in Fusion and Entry of T–Cell–Tropic Human Immunodeficiency Virus Type 1 Strains", J. Virol., 70(9):6288–6295 (1996).

Feng et al., "HIV–1 Entry Cofactor: Functional cDNA Cloning of a Seven–Transmembrane, G Protein –Coupled Receptor", Science, 272:872–877 (1996).

Hodge et al., "Humans with OKT4–Eptitope Deficiency Have a Single Nucleotide Base Change in the CD4 Gene, Resulting in Substitution of TRP$^{240}$ for ARG$^{240}$", Human Immunol., 30:99–104 (1991).

Kileen et al., "Regulated Expression of Human CD4 Rescues Helper T Cell Development in Mice Lacking Expression of Endogenous CD4", Embo J., 12(4):1547–1553 (1993).

MacKay, "Chemokine Receptors and T Cell Chemotaxis", J. Exp. Med., 184:799–802 (1996).

McCune et al., "Suppression of HIV Infection in AZT–Treated SCID–hu Mice", Science, 247:564–566 (1990).

Murphy, Annu. Rev. Immunol., "The Molecular Biology of Leukocyte Chemoattractant Receptors", 12:593–633 (1994).

(List continued on next page.)

Primary Examiner—Karen M. Hauda
Assistant Examiner—Anne Marie S. Beckerleg
(74) Attorney, Agent, or Firm—Finnegan, Henderson, Farabow, Garrett & Dunner

(57) ABSTRACT

This invention provides a transgenic mouse capable of expressing at least two cell surface membrane proteins of human T lymphocytes, transgenes for use in production of the transgenic mouse, and a method for producing the transgenic mouse using the transgenes. The cell surface membrane proteins of human T lymphocytes are associated particularly with human immunodeficiency virus (HIV) infection, and are preferably human CD4 and fusin (CXCR4). The transgenic mouse is able to inherit to its progeny a trait of expressing the cell surface membrane proteins of human T lymphocytes, thus being useful for an animal model for HIV infection and AIDS.

17 Claims, 3 Drawing Sheets

OTHER PUBLICATIONS

Nomura et al., "Molecular Cloning of cDNAs Encoding a LD78 Receptor and Putative Leukocyte Chemotactic Peptide Receptors", Int'l. Immunol., 5(10):1239–1249 (1993).

Oberlin et al., "The CXC Chemokine SDF–1 is the ligand for LESTR/fusin and Prevents Infection by T–Cell–Line–Adapted HIV–1", Nature, 382:833–835 (1996).

Sawada et al., "A Lineage–Specific Transcriptional Silencer Regulated CD4 Gene Expression During T Lymphocyte Development", Cell, 77:917–929 (1994).

Sawada et al., "Identification and Characterization of a T–Cell–Specific Enhancer Adjacent to the Murine CD4 Gene", Mol. Cell. Biol., 11(11):5506–5515 (1991).

Unutmaz et al., "Expression Pattern of HIV–1 Coreceptors on T Cells: Implications for Viral Transmission and Lymphocyte Homing", Proc. Nat'l. Acad. Sci. USA, 94:1615–1618 (1997).

Bates, P., "Chemoline Receptors and HIV–1: An Attractive Pair?" Cell, vol. 86, pp. 1–3 (1996).

Donda, A., et al., "Identification and characterization of a human CD4 silencer," Eur. J. Immunol., 26 vol. 493–500 (1996).

Sawada, S., et al., "Disturbed CD4+T cell homeostasis and in vitro HIV–1 susceptibility in transgenic mice expressing T cell line–tropic HIV–1 receptors," J. Exp. Med., vol. 187, No. 9, pp. 1439–1449 (1998).

Unutmaz et al. (1997) Proc. Natl. Acad. Sci. USA, vol. 94, 1615–1618, Mar. 1997.*

Berson et al. (1996) J. Virol., vol. 70 (9), 6288–6295, Sep. 1996.*

Sawada et al. (1998) J. Exp. Med., vol. 187 (9), 1439–1449, May 1998.*

* cited by examiner

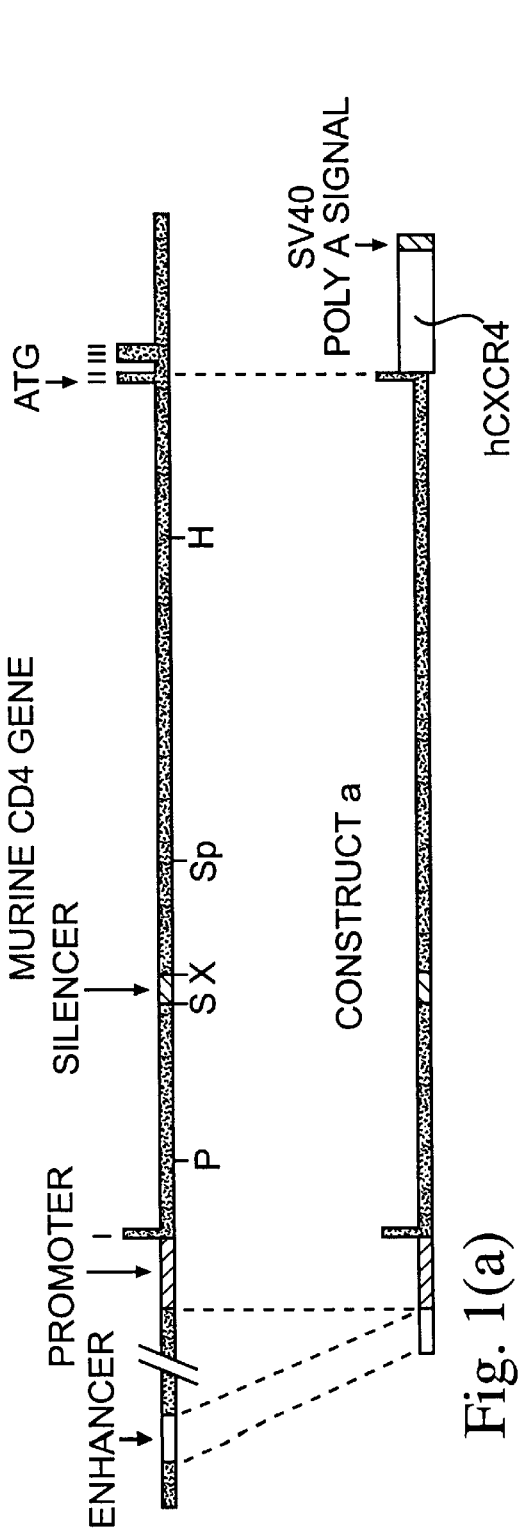
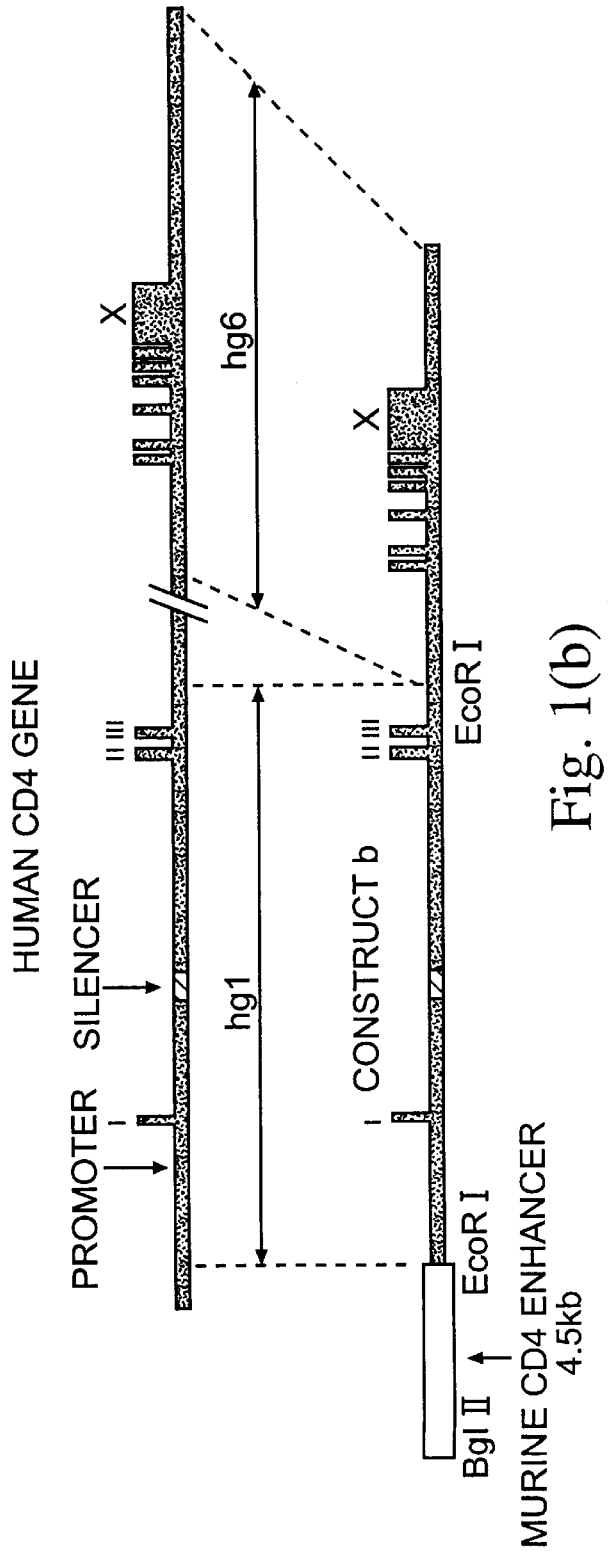
Fig. 1(a)
Fig. 1(b)

TRANSGENIC MOUSE EXPRESSING HUMAN FUSIN AND HUMAN CD4

BACKGROUND OF THE INVENTION

1. Field of the Invention

The present invention relates to an animal model for human diseases. More particularly, it relates to a transgenic mouse usable as an animal model for human acquired immunodeficiency syndrome (AIDS).

2. Disclosure of the Related Art

Human immunodeficiency virus (HIV) infection has spread throughout the world since 1981 when a patient with this infection was reported at the first time in the United State, and up to date, persons infected with HIV are presumed to exceed twenty millions. HIV infects human $CD4^+$ blood cells (i.e., helper T cell and macrophage) predominantly. The HIV infectious disease causes AIDS, which is characterized by decrease in $CD4^+$ T cells, after the latent period, thereby leading to death; that is, it is a disease that the prognosis is bad. Currently, no effective methods for prevention and treatment (e.g., vaccines) have been established, and the mechanism that HIV causes immunodeficiency has not yet been clarified.

One of the causes that make the solution of those problems late is that there exists no suitable small animal model for HIV infection. Anthropoids such as chimpanzees and monkeys have been utilized as animal models for HIV infection, whereas there are great demands on small animal models for HIV infection due to expensive management cost and limited facility.

Recently, the mouse that human blood cells have been transplanted in a hereditary immunodeficiency mouse (SCID mouse) so that the transplanted human blood cells could be infected with HIV has been developed as an animal model for HIV infection and has been used by some researchers (J. M. McCune et al., Science, 247:564–566, 1990).

However, when this mouse is used as an animal model for HIV infection, human blood cells must be transplanted in every individuals and HIV must be allowed to infect following settlement of the transplanted blood cells, i.e., several weeks after transplantation. Although SCID mouse is used to prevent the graft versus host (GVH) response following transplantation, the settlement of the transplanted human blood cells is insufficient or it does not occur sometimes. Thus, in cases where the SCID mouse is utilized in preparation of animal models for HIV infection, there are problems that preparation of such animal models needs the skill; that traits of individual mice are not constant with reflecting the efficiency of transplantation; and that no immunodeficiency is caused by HIV because HIV does not infect murine lymphocytes.

For the above reasons, there are great demands on small animal models for HIV infection, which are infected with HIV hereditarily; have constant traits; and are able to develop immunodeficiency seen in HIV infected patients.

In this situation, it has been reported in 1996 that when T-cell line tropic HIV strain invades T cells, fusin (or CXCR4) which is a cell surface protein of T lymphocytes is required as well as CD4 which is a other cell surface membrane protein of T lymphocytes (Y. C. Feng et al., Science (Wash. D.C.), 272:872–877, 1996; and J. F. Berson et al., J. Virol., 70:6288–6295, 1996).

The present inventor has continued to study actively in order to solve the above mentioned problems and, as a result, succeeded in production of a transgenic mouse in which at least two human T cell surface proteins are coexpressed on the surface of T lymphocytes of the mouse.

SUMMARY OF THE INVENTION

The present invention provides a transgenic mouse capable of pressing at least two cell surface membrane proteins of human T lymphocytes.

According to an embodiment of the present invention, the cell surface membrane proteins of human T lymphocytes are associated with HIV infection and are preferably CD4 and fusin (CXCR4). Genes encoding the cell surface membrane proteins of human T lymphocytes are integrated into the same chromosome of the mouse, preferably chromosomes in both gonocyte and somatic cells, and they are characterized by coexpression on the surface of murine $CD4^+$ T lymphocytes. In addition, the trait of expressing the cell surface membrane proteins of human T lymphocytes can be inherited from the transgenic mouse to its progeny.

According to a preferred embodiment of the present invention, there is provided a transgenic mouse in which human CD4 and fusin are coexpressed in $CD4^+$ T lymphocytes.

The present invention also provides a transgene comprising human fusin gene or human CD4 gene.

One of the transgenes comprises a transcriptional control region of murine CD4 gene, human fusin cDNA, and poly A addition signal in order in 5'→3'. The transcriptional control region may comprise, for example, murine CD4 enhancer, promoter, exon I, intron I, and part of exon II. Particularly, the transgene is Construct a shown in FIG. 1a.

Theother transgene comprises in 5'→3': a murine CD4 enhancer, and a modified human genomic CD4 gene with a modified human CD4 intron III in order. The modified human genomic CD4 gene preferably comprises about 3 kb region upstream of the human genomic CD4 gene and about 3 kb region downstream of the same. The modified human CD4 intron III is preferably composed of about 1.5 kb region at the 5'-side of human CD4 intron III and about 3 kb region at the 3'-side of the same. In other embodiment, the transgene is shown in FIG. 1b.

The present invention further provides a method for preparing a transgenic mouse, which comprises mixing together at least two different transgenes that comprise genes encoding at least two cell surface membrane proteins of human T lymphocytes; injecting the mixture into a murine fertilized egg; transplanting the obtained fertilized egg in a foster parent female mouse; allowing the transplanted mouse to breed; and selecting offspring mice that are able to express the at least two cell surface membrane proteins of human T lymphocytes. In this method, the cell surface membrane proteins of human T lymphocytes and the transgenes are both as defined above, and the former are particularly associated with HIV infection: human CD4 and human fusin in accordance with the embodiment of the present invention.

DETAILED DESCRIPTION OF THE DRAWINGS

Further details will be explained below with the help of the examples illustrated in the attached drawings in which:

FIG. 1(A & B) depicts construction of transgenes containing human genomic CD4 gene (modified) or human fusin cDNA, i.e., Construct a and Construct b, respectively;

DESCRIPTION OF THE PREFERRED EMBODIMENT

Figure 2:
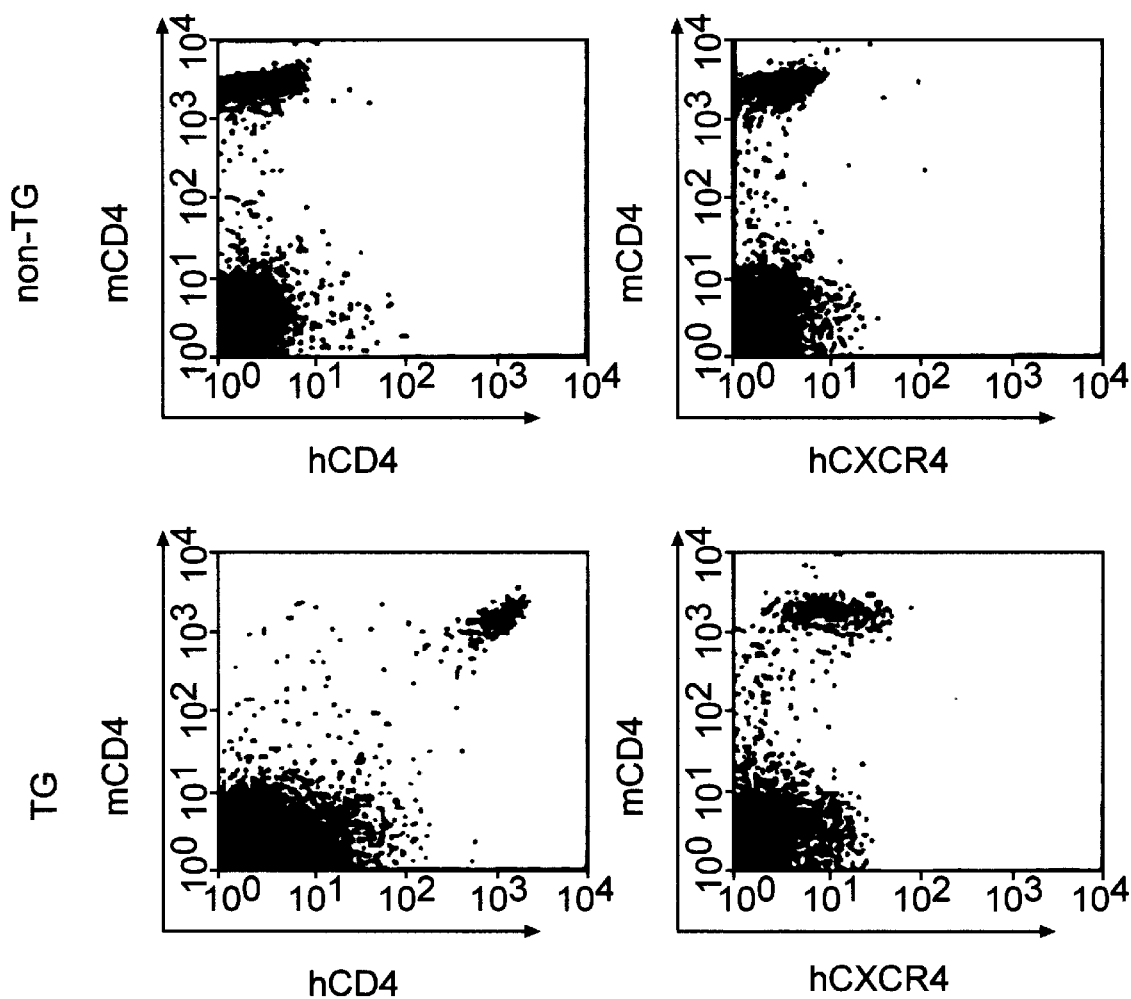
FIG. 2 depicts results of flow cytometry analyses for the expression of human CD4 and human fusin in peripheral lymphocytes of a transgenic mouse that genes for the CD4 and fusin have been introduced into.

In the present invention, the cell surface membrane proteins of human T lymphocytes capable of expressing on the surface of murine T lymphocytes include human CD4, CD8, CD25, CD44, fusin (or CXCR4), and the like (A. N. Barclay, "The Leukocyte Antigen Facts, Book," Academic Press). All of them are from human and therefore preferable in producing animal models that can be infected with human viruses including HIV. Fusin is known to be a receptor of CXC-chemokine SDF-1 (E. Oberlin et al., Nature, 382:833–835, 1996), and transmembrane chemokine receptors (e.g., fusin) function as chemotactic factors for hematopoietic lineage cells (C. R. Mackay, J. Exp. Med., 184:799–802, 1996). HIV includes macrophage-tropic and T cell line-tropic strains, and the former strain is associated with the latent period after infection while the latter strain with the development of AIDS. These HIV strains are known to utilize different chemokine receptors when invade human cells (P. M. Murphy, Annu. Rev. Immunol., 12:593–633; D. Unutmaz et al., Proc. Natl. Acad. Sci. USA, 94:1615–1618, 1997; and J. F. Berson et al., supra.). The transgenic mouse according to the present invention can express at least two cell surface membrane proteins of human T lymphocytes, which are associated with HIV infection, particularly infection with the T cell line-tropic strain. Because human CD4 and fusin are cell surface membrane proteins of T lymphocytes necessary for invasion of HIV into human T cells, it is preferred that they are coexpressed on the surface of murine $CD4^+$ T lymphocytes.

By expressing the above described cell surface membrane proteins suitably in murine T lymphocytes, transgenic mice usable as animal models for a variety of viral infections can be prepared.

In the present invention, genes encoding at least two cell surface proteins of human T lymphocytes can be introduced into chromosomes of both gonocyte and somatic cells. By this, the cell surface membrane proteins of human T lymphocytes are expressed on the surface of murine lymphocytes and stably transmitted hereditarily to progeny of the transgenic founder mouse. The term "gonocyte" used herein means a cell differentiated in individuals for the purpose of reproduction, and the term "somatic cell" is a corrective name of cells except gonocyte among cells forming individuals. Lymphocytes are formed via differentiation of the somatic cell.

Genes encoding at least two cell surface membrane proteins of human T lymphocytes are preferably introduced during embryogenesis. When they are introduced into the chromosome of a fertilized egg at the phase of cell division, traits derived from the transgenes are inherited to progeny according to the Mendel's law, thereby being able to conduct modification of murine characters. The embryogenesis means the early phase of ontogeny in multi-cellular animals.

The genes encoding at least two cell surface membrane proteins of human T lymphocytes can be obtained by screening cDNA or genomic DNA coding for membrane proteins such as CD4, CD8, CD25, CD44 and fusin using specific probes or antibodies; and amplifying them by known methods such as PCR. Alternatively, they may be synthesized chemically using a DNA synthesizer on the basis of data base information such as GenBank Accession No. M35160 (GenBank).

At least two DNA obtained above can be introduced into a murine embryo during embryogenesis by injecting them simultaneously into the nucleus of a fertilized egg using an injection needle. In this case, the genes of interest may be directly injected into the nucleus (particularly, pronucleus) of a fertilized egg, or alternatively transgenes carrying sequences such as suitable transcriptional control region (containing, for example, enhancer, promoter, silencer and the like) and poly A addition signal, the sequences being necessary for proper expression of the genes of interest on the murine genome, may be prepared and then injected into the nucleus of a fertilized egg. Injection can be performed using a microinjector, micromanipulator, or the like, preferably microinjector due to good efficiency of gene transfer and good operability. The genes of interest can be introduced into a fertilized egg separately or concurrently, preferably concurrently because time needed for introduction becomes shorter due to only one manipulation of introduction, and because the fertilized egg has less damage.

The term "transgene" used herein refers to a construct for introducing into the murine genome to prepare a transgenic mouse, the construct comprising a DNA sequence of a gene of interest to be introduced.

Transgene can comprise a transcriptional control region (containing, e.g. enhancer, promoter and silencer) allowing suitably to express genes for at least two cell surface membrane proteins of human T lymphocytes, poly A addition signal or the like, in addition to DNA sequences encoding at least two cell surface membrane proteins of human T lymphocytes such as CD4 and fusin. To express (transcribe) the above genes specifically in the body of a mouse, the murine transcriptional control region that comprises a promoter, an enhancer and a silencer is preferably contained at the upstream of a base sequence encoding the cell surface membrane protein of human T lymphocytes. It, however, is necessary to be previously confirmed that the transcriptional control region promotes the transcription suitably in chromatin of the nuclei of normal lymphocytes of a mouse.

The transgene according to the present invention may be linear or circular, preferably linear in view of the efficiency of integration in the chromosome of a mouse.

When transgenes for the expression of at least two cell surface membrane proteins of human T lymphocytes are constructed, they may be prepared so that genes encoding the at least two different membrane proteins are expressably contained together; or so that those different genes are contained separately.

Taking an example of the preparation of two transgenes that carry distinct genes encoding human CD4 and fusin, the present invention will be described in more detail.

The preparation of a transgene comprising human fusin cDNA (Construct a in FIG. 1a) can be conducted as described below.

Murine CD4 transcriptional control region that comprise CD4 enhancer, CD4 promoter and CD4 silencer, and SV40 derived poly A addition signal are prepared by excision of target regions from a cosmid containing murine CD4 gene (S. Sawada et al., Mol. Cell. Biol., 11:5506–5515, 1991) and a plasmid containing SV40 gene (e.g., pSV2 vectors; C. Gorman, DNA Cloning, Vol. II, p.144, IRL Press), 7 respectively, using suitable restriction endonucleases.

Human fusin cDNA can be prepared by PCR amplification from a human peripheral lymphocyte cDNA library (e.g., Human Peripheral Blood Leukocyte Quick-Clone™, Clontech) using, as primers, synthetic oligonucleotides made on the basis of sequences upstream and downstream of the fusin cDNA (H. Nomura et al., Int. Immunol., 5:1239–1249, 1993). The PCR method can in general be performed by repeating denaturation (94° C., about 30 sec –1 min), annealing (30–60° C., about 30 sec–1 min) and elongation (65–75° C., 2–5 min) for about 20 cycles or more in the presence of a heat-stable DNA polymerase like Taq polymerase (J. D. Watoson et al., "Recombinant DNA," second edition, pp.79–95, 1992, Scientific American Books).

The murine CD4 transcriptional control region and the SV40 poly A signal are ligated to the 5'- and 3'-ends of human fusin cDNA, respectively, by the conventional method (T. Maniatis et al., Molecular Cloning A Laboratory Manual (1989), second edition, Cold Spring Habor Laboratory Press), and the ligated product is then cloned into a suitable vector to give Construct a as shown in FIG. 1a.

Another transgene comprising human CD4 gene (Construct b in FIG. 1b) can be prepared as described below.

The human CD4 gene can be prepared from a commercially available human genomic library (e.g., human genomic library, Clontech) in the similar manner as above on the basis of the known nucleic acid sequence of human CD4 gene as described by N. Killeen et al. in EMBO J., 12:1547–1553, 1993. The obtained human CD4 gene is then cleaved into about 1.5 kb region at 5'-side of the intron III and about 3 kb region at 3'-side of the intron III using suitable restriction endonucleases, after which the 5' and 3' regions are cloned into distinct plasmids and ligated together to yield a modified intron III. The modified human CD4 gene can thus comprise the transcriptional control region containing human CD4 promoter and human CD4 silencer (which is in fact included in human CD4 intron I), all human CD4 exons, all human CD4 introns except part of intron III, and about 3 kb region downstream of human CD4 gene. Because the intron III has a size over 20 kb, the efficiency of injection or introduction decreases if a transgene carrying the entire intron III is prepared. The part of intron III is therefore removed preferably.

The murine CD4 enhancer can also be prepared in the similar manner on the basis of its known nucleic acid sequence (S. Sawada et al., Mol. Cell Biol., 11:5506–5515, 1991). The enhancer is contained in about 4.5 kb BglII-EcoRI fragment (see FIG. 1b).

The murine CD4 enhancer is ligated to the 5'-end of the modified human CD4 gene by the conventional method, and the ligated product is then cloned into a suitable vector to give Construct b as shown in FIG. 1b.

The two constructs so prepared above can be used to produce a transgenic mouse as follows:

The cloned constructs are treated with suitable restriction endonucleases, thereby removing the corresponding vector portions. The inserts are completely separated from each vector portion by agarose gel electrophoresis, and they are extracted from each gel. The resulting constructs are prepared into a solution with a concentration of 1–10 μg/ml after purification.

The solutions containing Constructs a and b are subsequently mixed together and injected in a level of 1–2 μl into a murine fertilized egg using a microinjector.

Mice used in production of transgenic mice include, but are not limited to, BDF1, CDF1, DBA/2, C57BL/6(B6) and so forth. BDF1 is preferable in view of the number of ovulation, percentage of coitus, etc. Furthermore, to examine whether the trait of a transgenic mouse is inherited stably to the progeny, mice such as C57BL/6, DBA/2 and BDF1 are usable with preference of C57BL/6 which has a benefit that analyses are easier.

Lymphocytes comprise B lymphocyte associated with humoral immunity and T lymphocyte associated with cell-mediated immunity, and through expression of the above mentioned at least two human cell surface membrane proteins on the T lymphocytes of mice, the transgenic mouse of the present invention can be prepared as an animal model for infection with a T cell line-tropic HIV strain such as strains Lai, IIIB or BH8.

Of the mice treated as above using the two constructs, mice in which the genes or cDNA for human CD4 and fusin have been integrated into the same chromosome is selected. As the two genes are integrated in the same chromosome of the transgenic mice, they are transmitted concurrently to a litter of mice and their traits are inherited stably to the progeny in accordance with the Mendel's law.

The offspring mice can therefore acquire the same traits as their parents, thereby being able to prepare mice with constant traits. And the obtained transgenic mice can be used to conduct any researches with extremely high reproducibility.

The detection of the human genes introduced into the embryo of a transgenic mouse or its offspring can be conducted by taking DNA from their tails and analyzing by Southern hybridization using $^{32}$P-DNA that were labeled using polynucleotide kinase (M. Kriegler, "Gene Transfer and Expression, A Laboratory Manual," Freeman and Company). Further, the tissue-specific expression of human CD4 and fusin can be tested by fluorescence immunoassay (flow cytometry), in situ RT-PCR, in situ immune staining, Northern blotting, or the like (M. Kriegler, supra).

Whether the human cell surface proteins have been expressed in murine peripheral and thymus T lymphocytes can be confirmed through separation of T lymphocytes from the murine peripheral blood and thymus, by a method such as extraction of RNA from T cells or by fluorescence immunoassay using fluorescence-labeled monoclonal antibodies. Use of the fluorescence immunoassay is preferred because the operation is simple and the obtained result is precise.

When the fluorescence immunoassay is used, commercially available anti-human CD4 antibodies may be employed, or alternatively anti-human CD4 polyclonal or monoclonal antibodies obtainable by immunity of a human CD4 antigen in an animal by known methods (e.g., G. K öhler and G. Milstein, Nature, 256:495, 1975; and T. Iwasaki et al., "Monoclonal antibody, Hybridoma and ELISA" (1987), Kodan-sha Scientific, Japan). The anti-human CD4 monoclonal antibody is commercially available from DAKO (Denmark; MT310). Anti-fusin monoclonal antibody is also available from Pharmingen (San Diego, Calif.; 12G5). These antibodies can be labeled with FITC (fluorescein isothiocyanate), PE (phycoerythrin), TRI-COLOR™ (also called TC; Caltag Laboratory, CA) or the like. Anti-human CD4 and anti-human fusin antibodies may be used alone or in combination with any other antibodies.

The expression of human CD4 and human fusin in murine T lymphocytes can be tested by flow cytometry (e.g., using FACS™, Becton Dickinson Immunocytometry Systems, CA) after the fluorescence-labeled monoclonal antibody is reacted with T lymphocytes from the transgenic mouse or its offspring. In either anti-human CD4 monoclonal antibody or anti-human fusin monoclonal, the increase in strength of fluorescence in comparison with control is an indication of the expression of the T lymphocyte surface membrane proteins. If anti-murine CD4 and CD8 antibodies (available from Pharmingen, Calif.) are added concurrently to the above reaction, the subset of T lymphocytes that expresses human CD4 and human fusin can be identified by the tri-color flow cytometory. The combination of such antibodies includes: anti-human CD4-FITC, anti-murine CD4-PE and anti-murine CD8-TRICOLOR; and anti-human fusin+ anti-murine IgG2a-FITC, anti-murine CD4-PE and anti-murine CD8-TRICOLOR.

As in human CD4 and fusin, genes that code for other cell surface membrane proteins of human T lymphocytes, such as CD8, CD25 and CD44, can be introduced into the same or different transgenes to be integrated in the murine chromosome, and subsequently injected into a murine fertilized egg. Genomic DNA or cDNA for CD8, CD25 or CD44 is described by A. N. Barclay et al. in "The Leukocyte Antigen Facts, Book," Academic Press.

In the transgenic mouse according to the present invention, the human CD4 and human fusin are both expressed specifically in murine CD4$^+$ T lymphocytes as illustrated in the following Examples. The CD4$^+$ T lymphocytes can therefore be infected with HIV and provides a state very similar to human HIV infection in which human CD4$^+$ T lymphocytes are a target. The transgenic mouse can be used to make an animal model for HIV infection; to study mechanisms of the HIV infection and development of AIDS; or to develop various methods for the treatment and prevention, particularly antiviral agents, gene therapy, vaccines and so on. In addition, it has now been found that the CD$^+$ T cell count is decreased in peripheral blood of the mouse even if the mouse is not infected with HIV-1. Thus the transgenic mouse has a phenotype similar to the conditions of AIDS seen in the late phase of HIV-1 infection in human. This mouse is therefore expected to be helpful for elucidation of a mechanism of the development of AIDS.

The present invention will be illustrated in more detail by the following Examples, but it should be understood that those examples are illustrative and are not intended to limit the present invention.

EXAMPLES

Example 1

Preparation of Transgenes (Constructs a and b)

Two constructs (i.e., transgenes) shown in FIG. 1 were prepared. First, human fusin gene (CXCR4) was obtained as set forth below.
(1) Preparation of Human Fusin Gene (CXCR4)

The human fusin gene was prepared by PCR amplification from human peripheral lymphocyte cDNA library (Human Peripheral Blood Leukocyte Quick-Clone™, Clontech, Palo Alto, Calif.) by using the following primers:

5'-TGAGTCGACTGAGTGCTCCAGTAGCCACC-3' (SEQ ID NO:1); and

5'-TAGGTCGACAGATCTTGTACAATATTGGTCAG-TCTT-3' (SEQ ID NO:2), which were synthesized on the basis of the sequences upstream and downstream of human fusin cDNA (H. Nomura et al., Int. Immunol., 5:1239–1249, 1993). In PCR, the cycle of 94° C., 1 min; 55° C., 1 min; and 72° C., 3 min was repeated for 30 cycles, followed by 72° C., 15 min. The enzyme and buffer used in PCR were cloned Pfu DNA polymerase in combination with buffer (Stratagene, La Jolla, Calif.).

(2) Preparation of Construct a

In FIG. 1a there are illustrated a murine CD4 gene and a transgene (i.e., Construct a).

HindIII genomic fragment that contains exons II and III of murine CD4 was cleaved out from the murine cosmid clone Cosmid 6 (S. Sawada et al., Mol. Cell. Biol., 11:5506–5515, 1991) and subcloned into pBluescript KS(–). The translational initiation codon was removed from exon II by site-directed mutagenesis, and then SalI and NotI sites were introduced into the remainder. The resulting NotI fragment comprises a part of intron I and a non-translational region of exon II.

The NotI fragment was subcloned into NotI sites of pNNO3 vector (S. Sawada et al., supra) wherein the pNNO3 is a PUC18 vector with modified polylinker, namely, having NotI sites at both ends of the polylinker.

From plasmid pDD2 carrying SV40 gene (S. Sawada et al., Cell, 77:917–929, 1994), the ClaI-NotI fragment that contains an SV40 polyadenylation site was cleaved out using ClaI and NotI. This fragment was blunt-ended with Klenow DNA polymerase I, and subsequently was inserted into SalI sites of pNNO3 that has previously been blunt-ended with the same enzyme, resulting in that the SalI sites were reconstituted.

The SalI fragment that contains the cDNA for hCXCR4 prepared as in the above (1) was then inserted into the reconstituted SalI sites of pNNO3 to yield a plasmid.

Next, Cosmid 6 was treated with HindIII to separate a fragment containing 5' flanking region, exon I and part of intron I, all of which were derived from murine CD4, followed by insertion of the fragment into the HindIII sites of the plasmid obtained above. The 5' flanking region upstream of a KpnI site of the exon I inserted at the HindIII sites of the plasmid was subsequently replaced with an XbaI-KpnI fragment (487 bp) of murine CD4, which contains the smallest promoter.

339 bp of the smallest enhancer of murine CD4 was inserted at the EcoRI site of the 5' end of the resulting plasmid which has been cleaved with EcoRI, thereby yielding Construct a.

In the preparation of Construct a, all the ligations of genes were conducted using T4 DNA ligase.

The murine CD4 gene shown in FIG. 1a comprises an enhancer, a promoter, and exon I to the upstream portion of exon II, wherein ATG is a translational initiation site.

Construct a shown in FIG. 1 is the ligated product of the murine CD4 transcriptional control region (i.e., upstream region of murine CD4 gene, containing CD4 enhancer and CD4 promoter), exon I, intron I, part of exon II, and human fusin (CXCR4) cDNA, which were ligated in order in 5'→3'. At the 3'-end of fusin cDNA, Sv40 poly A addition signal was ligated (FIG. 1a).

In FIG. 1a, I, II and III represent exons, and P, S, X, Sp and H are recognition sites of the restriction enzymes PstI, SacI, XbaI, SphI and HindIII, respectively. As to PstI and SacI, all sites thereof are not depicted therein.
(2) Preparation of Construct b To prepare Construct b, the human CD4 gene was screened from human genomic library (λ phage library; Clontech) using a specific probe.

In preparation of Construct b, two plasmids (pUC13) i.e. Puc/hg1 and Puc/hg6, in which the human CD4 gene has been inserted into their EcoRI sites, were employed (FIG. 1b). Puc/hg1 contained about 3 kb region upstream of the 5' end of human CD4 gene, exon I, intron I, exon II, intron II, exon III, and about 1.5 kb region at the 5'-side of intron III, these exons and introns being derived from the human CD4 gene. Puc/hg6 contained about 3 kb region at the 3'-side of human CD4 intron III, human CD4 exon IV, human CD4 intron IV to exon X, and about 3 kb region downstream of the human CD4 gene.

From the Puc/hg1 and Puc/hg6, two fragments shown in FIG. 1 were obtained using EcoRI digestion. The resulting two fragments were ligated together using T4 ligase, and then cloned into another plasmid pNNO3 (S. Sawada et al., Cell, 77:917–929, 1994), resulting in modification of the human CD4 gene. As a result, most of the intron III was removed from the native human CD4 gene (FIG. 1b).

The modified human CD4 gene contained the transcriptional control region of human CD4 gene (i.e., about 3 kb region comprising the CD4 promoter), all exons of human CD4 gene, all introns of human CD4 gene excepting part of intron III, and the about 3 kb region downstream of human CD4 gene.

Enhancer of murine CD4 gene was cleaved out from the murine cosmid clone (Cosmid 6) using BalII and EcoRI. It had a size of 4.5 kb and an enhancer activity as determined by reporter assay (M.C.B., 11(No.11):5506–5516, 1991).

The resulting murine CD4 enhancer was then ligated to the 5' end of the modified CD4 gene using T4 ligase (FIG. 1b).

(3) Purification of Constructs a and b

Constructs a and b that were prepared in Examples 1 and 2, respectively, were treated with NotI to separate into each vector portion and each insert. After isolated and purified by agarose gel electrophoresis, each insert so obtained was prepared into a solution with a concentration of 10 μg/ml.

Example 2

Production of Trangenic Mouse (1) Obtainment and Manipulation of Fertilized Egg

Five units of PMSG (pregnant mare serum gonadotropin) was administered to BDF1 mice (female, 4–6 week old). After 48 hours, 5 units of HCG (human chorionic gonadotropin) was further administered to the mice in order to induce overovulation so that they copulated with male mice. Next date, the copulation was confirmed and subsequently the oviducts with part of uterus were excised from the female mice, from which fertilized eggs were obtained in a culture medium containing 1 mg/ml of hyaluronidase.

Next, the solution having Constructs a and b was injected into the nucleolus of the murine fertilized eggs using a microinjector.

(2) Production of Transgenic Mouse

The fertilized egg that Constructs a and b have been introduced into as described in the above (1) was injected within the oviduct of a faster parent mouse (BDF1, 6–15 week old). This mouse was then raised to the end of the pregnancy period in a facility with controlled environment, after which whether the two constructs were integrated in genomes of offsprings of the mouse was examined.

(3) Confirmation of Gene Transfer to Mouse

Whether the two constructs were integrated in 4-week-old new born mice of the provisional parent mouse was tested as follows.

Tails were removed from the new born mice in order to obtain DNAs which were then analyzed by Southern hybridization using $^{32}$P-DNA probes that were labeled using polynucleotide kinase. The probes were synthesized on the basis of the known nucleic acid sequences of human CD4 cDNA (T. W. Hodge et al., Hum. Immunol., 30:99–104, 1991) and human fusin cDNA (H. Nomura et al., Int. Immunol., 5:1239–1249, 1993), namely they are:

5'-ATGAACCGGGGAGTCCCTTTT-3' (SEQ ID NO:3); and

5'-TGAGTGCTCCAGTAGCCACC-3' (SEQ ID NO:4).

T lymphocytes obtained from the transgenic mice were tested for expression of human CD4 and human fusin using fluorescence-labeled monoclonal antibodies: FITC labeled anti-human CD4 monoclonal antibody MT310 (purchased from DAKO, Glostrup, Denmark) and anti-human fusin monoclonal antibody 12G5 (kindly provided by Dr. James A. Hoxie of Pennsylvania University). The antibody 12G5 is commercially available from Pharmingen (San Diego, Calif.), etc., too.

These labeled antibodies were reacted with lymphocytes from the newborn mice at 4° C. for about 30 min. The antibody 12G5 was further reacted with anti-mouse IgG2a-FITC (Pharmingen). The change in profile of the fluorescence strength depending on binding to the antibodies was examined by flow cytometry and was compared with results from control mice.

On the basis of the results of flow cytometry analyses, newborn mice that both Constructs a and b have been introduced into were selected as double transgenic mice. And, based on the fluorescence strength determined, mouse #12 (male) was obtained in which the two proteins were expressed in the largest amounts (Table 1).

TABLE 1

Expression of transgenes in murine CD4+ T lymphocytes

| | Expression of transgenes[1] | |
|---|---|---|
| Founders | Human CD4 | human fusin |
| #6 | + | − |
| #12 | + | + |
| #20 | + | +/−[2] |
| #46 | + | − |

[1]Lymphocytes of offspring mice that were born by breeding founders (BDGF1) with B6 mice were analyzed by the flow cytometry method.
[2]The expression of human fusin in the offspring #20 was not seen in peripheral CD4+ T lymphocytes but thymus CD4+ T lymphocytes.

Example 3

Confirmation of Stability of Traits Introduced by Transgenes

Mouse #12 was bred with C57BL/6J female mice, and tails of newborn mice were taken to obtain DNA therefrom. The DNA was analyzed in the same way as in Example 2.

Expression of human CD4 and human fusin was analyzed in protein level by flow cytometry in the same way as in Example 2, wherein the anti-human CD4 and anti-human fusin monoclonal antibodies used were MT3310 and 12G5, respectively. The expression of the transgenes are shown in FIGS. 2 and 3.

Figure 3:
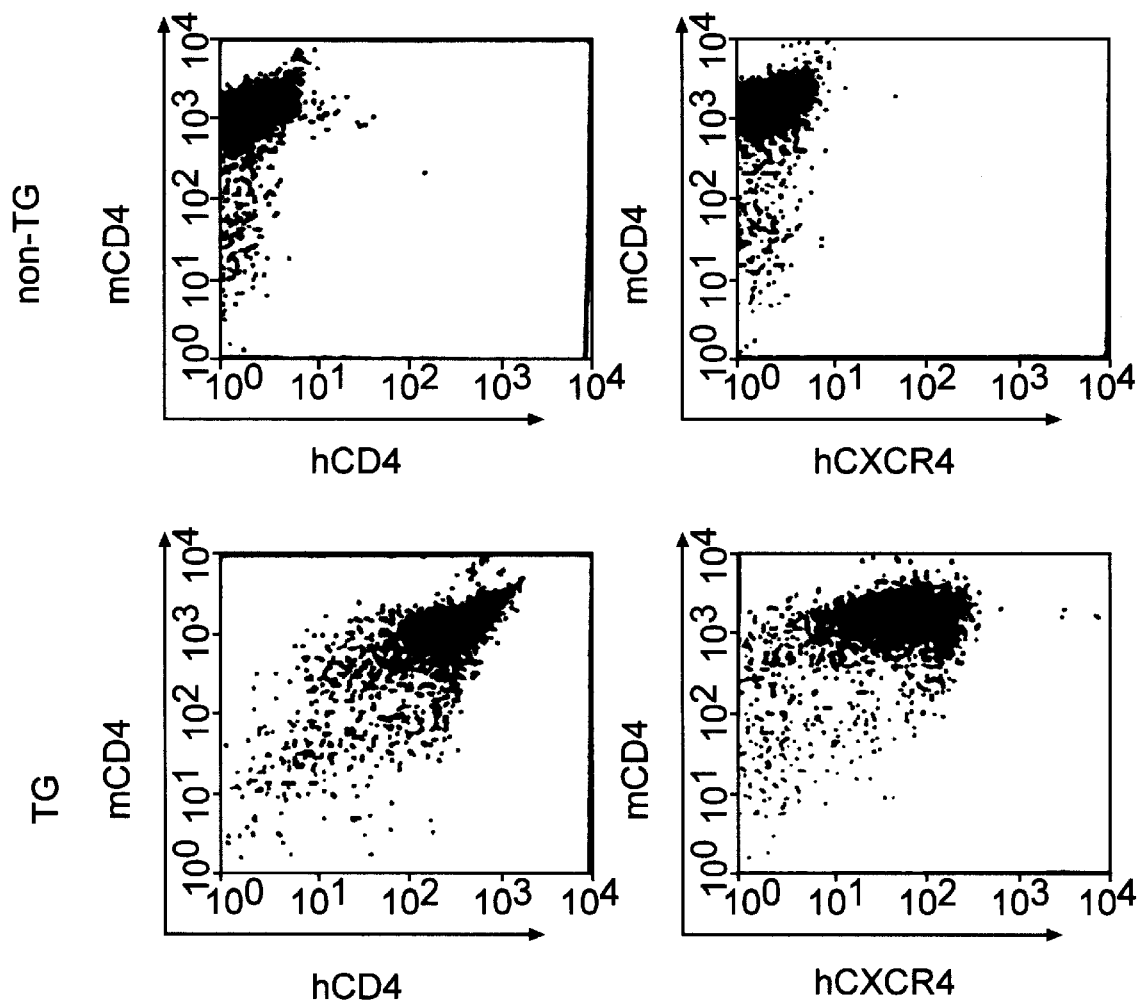
FIG. 3 depicts results of flow cytometry analyses for the expression of human CD4 and human fusin in thymocytes of a transgenic mouse that genes for the CD4 and fusin have been introduced into.

In FIGS. 2 and 3, the upper plates show results of the flow cytometry of human CD4 ("hCD4") and human fusin ("hCXCR4") in non-transgenic mice as control ("non-TG"), while the lower plates show results in transgenic mice ("TG"). And FIG. 2 is the expression in murine peripheral lymphocytes, and FIG. 3 is the expression in murine thymocytes. These cells were tested by the tri-color flow cytometry using a set of anti-human CD4-FITC (DAKO), anti-mouse CD4-PE (Pharmingen) and anti-human CD8-TRICOLOR™ (Caltag, Burlingame, Calif.) or another set of anti-human fusin+anti-mouse IgG2a-FITC (Pharmingen), anti-mouse CD4-PE and anti-mouse CD8-TRICOLOR™.

As seen in FIGS. 2 and 3, the results of flow cytometry analyses for expression of human CD4 and human fusin in lymphocytes of the transgenic and non-transgenic mice indicate that the human CD4 and fusin were both expressed in the transgenic mouse.

Furthermore, as seen from the tri-color flow cytometry analyses in FIGS. 2 and 3, the expression of the human proteins was limited to murine peripheral CD4+ T lymphocytes and murine thymus CD4+ T lymphocytes, indicating that this expression was tissue-specific and was due to effect of the CD4 transcriptional control region contained in Constructs a and b. Such effect was observed in both the murine peripheral (FIG. 2) and thymus (FIG. 3) lymphocytes.

It was thus demonstrated that the CD4+ T lymphocytes of the transgenic mice coexpressed human CD4 and fusin molecules on the surface of the lymphocytes. The amounts of the two molecules expressed were larger than those in human CD4+ T lymphocytes (data not shown).

In conclusion, in CD4+ T lymphocytes of transgenic mouse #12 and its offspring, the human CD4 and fusin were coexpressed. Therefore, in the transgenic mice both the Constructs a and b were introduced without exception, and they were integrated into the same chromosome. This trait is thought to be transmitted concurrently to the progeny of the mouse according to the Mendel's law.

In the present invention, it should be understood that to the extent any disclosed modifications or alterations may not literally fall within the scope of the appending claims, they are considered to be part of the invention under the doctrine of equivalents.

What is claimed is:

1. A transgenic mouse whose genome comprises:
    a first transgene comprising a transcriptional control region operably linked to cDNA encoding human fusin (CXCR4), wherein said control region comprises a murine CD4 promoter;
    a second transgene comprising a transcriptional control region operably linked to DNA encoding human CD4, wherein said control region comprises a CD4 promoter; and
        wherein said transgene comprises at least one member of the group consisting of a murine CD4 promoter and a modified human CD4 intron III;
    wherein the transgenes are co expressed on the surface of CD4+T lymphocytes.

2. The transgenic mouse of claim 1 wherein the first transgene further comprises a CD4 enhancer.

3. The transgenic mouse of claim 1 wherein the first transgene further comprises a CD4 silencer.

4. The transgenic mouse of claim 1 wherein the first transgene further comprises a CD4 enhancer and CD4 silencer.

5. The transgenic mouse of claim 1 wherein the first transgene comprises the murine CD4 enhancer, promoter, exon I, intron I, and part of exon II, as shown in Construct a of FIG. 1(a).

6. The transgenic mouse of claim 1 wherein the second transgene further comprises a CD4 enhancer.

7. The transgenic mouse of claim 1 wherein the second transgene further comprises a CD4 silencer.

8. The transgenic mouse of claim 1 wherein the second transgene further comprises a modified human CD4 intron III.

9. The transgenic mouse of claim 1 wherein the second transgene further comprises a CD4 enhancer, CD4 silencer, and a modified human CD4 intron III.

10. The transgenic mouse of claim 1 wherein the second transgene further comprises a human CD4 promoter, murine CD4 enhancer, human CD4 silencer, and a modified human CD4 intron III, as shown in Construct b of FIG. 1(b).

11. The transgenic mouse of claim 1 wherein the first and second transgenes are integrated into the same chromosome.

12. A transgene comprising a transcriptional control region operably linked to cDNA, encoding human fusin (CXCR4), wherein said control region comprises the murine CD4 promoter.

13. The transgene of claim 12 wherein said control region further comprises a CD4 enhancer.

14. The transgene of claim 12 wherein said control region further comprises a CD4 silencer.

15. The transgene of claim 12 wherein said control region further comprises a CD4 enhancer and CD4 silencer.

16. A transgene comprising a transcriptional control region operably linked to DNA encoding human CD4, wherein said control region comprises a CD4 promoter, a CD4 enhancer, a CD4 silencer, and a modified human CD 4 intron III.

17. A method for producing a transgenic mouse whose genome comprises human CD4 and human fusin comprising:
    a) injecting into a fertilized mouse egg:
        a transgene comprising a transcriptional control region operably linked to cDNA encoding human fusin (CXCR4), wherein said control region comprises the murine CD4 promoter; and
        a transgene comprising a transcriptional control region operably linked to DNA encoding human CD4, wherein said control region comprises the CD4 promoter; and
            wherein said transgene comprises at least one member of the group consisting of a murine CD4 promoter and a modified human CD4 intron III;
    b) transplanting the injected egg in a foster parent female mouse;
    c) selecting a mouse derived from an injected egg whose genome comprises human CD4 and human fusin, that coexpresses the human CD4 and human fusin on the surface of CD4+T lymphocytes.

* * * * *

```
                             SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
         (A) LENGTH: 29 base pairs
         (B) TYPE: nucleic acid
         (C) STRANDEDNESS: single
         (D) TOPOLOGY: linear (ii) MOLECULE TYPE: Other nucleic acid (xi) SEQUENCE DESCRIPTION: SEQ ID NO:1:

TGAGTCGACT GAGTGCTCCA GTAGCCACC                                            29

(2) INFORMATION FOR SEQ ID NO:2:

(i) SEQUENCE CHARACTERISTICS:
         (A) LENGTH: 36 base pairs
         (B) TYPE: nucleic acid
         (C) STRANDEDNESS: single
         (D) TOPOLOGY: linear (ii) MOLECULE TYPE: Other nucleic acid (xi) SEQUENCE DESCRIPTION: SEQ ID NO:2:

TAGGTCGACA GATCTTGTAC AATATTGGTC AGTCTT                                    36

(2) INFORMATION FOR SEQ ID NO:3:

(i) SEQUENCE CHARACTERISTICS:
         (A) LENGTH: 21 base pairs
         (B) TYPE: nucleic acid
         (C) STRANDEDNESS: single
         (D) TOPOLOGY: linear (ii) MOLECULE TYPE: Other nucleic acid (xi) SEQUENCE DESCRIPTION: SEQ ID NO:3:

ATGAACCGGG GAGTCCCTTT T                                                    21

(2) INFORMATION FOR SEQ ID NO:4:

(i) SEQUENCE CHARACTERISTICS:
         (A) LENGTH: 20 base pairs
         (B) TYPE: nucleic acid
         (C) STRANDEDNESS: single
         (D) TOPOLOGY: linear
```

```
        (ii) MOLECULE TYPE: Other nucleic acid (xi) SEQUENCE DESCRIPTION: SEQ ID NO:4:

TGAGTGCTCC AGTAGCCACC                                              20
```